(12) United States Patent
Gao et al.

(10) Patent No.: US 10,835,553 B2
(45) Date of Patent: Nov. 17, 2020

(54) APPLICATION OF HYDROXYPROPYL METHYL CELLULOSE IN PREPARATION OF MEDICINE FOR TREATMENT OF ESOPHAGEAL MUCOSA

(71) Applicant: Hefei Jiu Yan Medicine Technology Development Co., Ltd., Anhui (CN)

(72) Inventors: Yu Gao, Anhui (CN); Yunli Bu, Anhui (CN)

(73) Assignee: Hefei Jiuyan Pharmaceutical Science and Technology Development Co., Ltd., Heifei (CN)

( * ) Notice: Subject to any disclaimer, the term of this patent is extended or adjusted under 35 U.S.C. 154(b) by 0 days.

(21) Appl. No.: 16/247,540

(22) Filed: Jan. 14, 2019

(65) Prior Publication Data

US 2019/0142859 A1 May 16, 2019

Related U.S. Application Data

(63) Continuation of application No. PCT/CN2017/092090, filed on Jul. 6, 2017.

(30) Foreign Application Priority Data

Jul. 12, 2016 (CN) .......................... 2016 1 0546792

(51) Int. Cl.
| | |
|---|---|
| *A61K 31/717* | (2006.01) |
| *A61P 1/04* | (2006.01) |
| *A61K 47/26* | (2006.01) |
| *A61K 47/12* | (2006.01) |
| *A61K 47/36* | (2006.01) |
| *A61K 47/42* | (2017.01) |
| *A61K 47/02* | (2006.01) |
| *A61K 47/14* | (2017.01) |
| *A61P 1/02* | (2006.01) |
| *A61K 9/08* | (2006.01) |
| *A61K 47/38* | (2006.01) |

(52) U.S. Cl.
CPC ............. *A61K 31/717* (2013.01); *A61K 9/08* (2013.01); *A61K 47/02* (2013.01); *A61K 47/12* (2013.01); *A61K 47/14* (2013.01); *A61K 47/26* (2013.01); *A61K 47/36* (2013.01); *A61K 47/38* (2013.01); *A61K 47/42* (2013.01); *A61P 1/02* (2018.01); *A61P 1/04* (2018.01)

(58) Field of Classification Search
None
See application file for complete search history.

(56) References Cited

U.S. PATENT DOCUMENTS

2002/0103219 A1* 8/2002 Jacob ..................... A61K 9/006
514/291
2008/0096978 A1* 4/2008 Tsao ..................... A61K 9/0048
514/781

OTHER PUBLICATIONS

Bu, CN 105342897, Feb. 2016, machine translation. (Year: 2016).*

* cited by examiner

*Primary Examiner* — Layla D Berry
(74) *Attorney, Agent, or Firm* — Wayne & Ken, LLC; Tony Hom

(57) ABSTRACT

The invention discloses an application of hydroxypropyl methyl cellulose in preparation of medicines for treating esophageal mucosa. The invention discloses a hydroxypropyl methyl cellulose-containing composition which comprises the following ingredients: 1-28 weight parts of hydroxypropyl methyl cellulose and 1000 weight parts of purified water. A preparation method includes steps of adding the hydroxypropyl methyl cellulose, by stirring, into the purified water in an amount which accounts for 40% of the total amount of water used to obtain a mixed material, continuously stirring the mixed material until the mixed material is completely swelling and turning into a transparent solution, adding the remaining purified water to obtain a mixture, and stirring the mixture to obtain the hydroxypropyl methyl cellulose-containing composition. The hydroxypropyl methyl cellulose and the hydroxypropyl methyl cellulose-containing composition-contained composition in the invention generate a membrane in esophagus, and the generated membrane has adhesion and therefore works continuously.

4 Claims, No Drawings

APPLICATION OF HYDROXYPROPYL METHYL CELLULOSE IN PREPARATION OF MEDICINE FOR TREATMENT OF ESOPHAGEAL MUCOSA

CROSS-REFERENCE TO RELATED APPLICATIONS

This application is a continuation of International Patent Application No. PCT/CN2017/092090, filed on Jul. 6, 2017, which claims the benefit of priority from Chinese Application No. 2016/10,546,792.1, filed on Jul. 12, 2016. The entire contents of the aforementioned applications, including any intervening amendments thereto, are incorporated herein by reference.

TECHNICAL FIELD

The invention relates to an application of hydroxypropyl methyl cellulose in the treatment of esophageal mucosa injuries.

BACKGROUND

The esophagus is a long muscular conduit, with a whole length of 25-30 cm. The esophagus has three narrow parts. Foreign substances are usually retained at the three narrow parts. Therefore, esophageal cancer is usually found at the three narrow parts. The esophagus has a primary function of delivering food into the stomach and also has the functions of preventing air from entering the stomach when a person is breathing and preventing contents in the stomach from flowing back.

All physiological functions of the esophagus are conducted with the help of mucosa, and mucosa is easily injured. Mucosa injuries tend to induce infections and result in mucosal abscesses, affecting the normal physiological functions of the esophagus. At present, esophageal mucosa injuries are usually treated with antiphlogistic medicines. However, due to particular positions, gastrointestinal tract administration, injection and intravenous injection are usually adopted during treatment. In the majority cases, patients are systemically administered with a large amount of medicines. The medicines cannot be directly applied to partially injured mucosa, and work slowly.

SUMMARY

The first objective of the invention is to provide an application of hydroxypropyl methyl cellulose in the treatment of esophageal mucosa injuries. Hydroxypropyl methyl cellulose has long-lasting shielding, protective, bacteriostatic and pain-killing actions when used to treat esophageal mucosa injuries.

The second objective of the invention is to provide a hydroxypropyl methyl cellulose-containing composition for treatment of esophageal mucosa injuries.

The third objective of the invention is to provide a preparation method of the composition.

The fourth objective of the invention is to provide an application of the composition.

The objectives of the present invention can be fulfilled by the following technical solution:

When used to treat esophageal mucosa injuries, hydroxypropyl methyl cellulose has long-lasting shielding, protective, bacteriostatic and pain-killing actions.

Further, hydroxypropyl methyl cellulose may also be a hydroxypropyl methyl cellulose-containing composition, and the composition includes the following ingredients in part by weight: 1-28 parts of hydroxypropyl methyl cellulose and 1000 parts of purified water.

Further, the hydroxypropyl methyl cellulose-containing composition may also include the following ingredients in part by weight: 1-10 parts of sodium carboxymethylcellulose, 30-150 parts of glycerinum, 0.3-20 parts of stabilizer and 0.001-0.1 parts of essence.

The sodium carboxymethylcellulose may be replaced by maltodextrin. More further, the hydroxypropyl methyl cellulose-containing composition may also include the following ingredients in part by weight: 1-90 parts of sodium bicarbonate, 10-40 parts of xylitol, 0.1-6 parts of citric acid, 2-9 parts of potassium hydroxide, 2-10 parts of phosphoric acid, and 0.1-2 parts of sodium benzoate.

The aforementioned hydroxypropyl methyl cellulose-containing composition may also include 10-40 weight parts of polydextrose.

The stabilizer used in the invention is one or a mixture of several ones of polysorbate, sorbitol fatty acid esters, monoacylglyceride, Arabic gum, gelatin and yolk.

A method for the preparation of the hydroxypropyl methyl cellulose-containing composition for treating esophageal mucosa includes the following steps:

step 1, adding the hydroxypropyl methyl cellulose into the purified water by stirring in an amount which accounts for 40% of the total amount of water used to obtain a mixed material, continuously stirring the mixed material until the mixed material is completely swelling and turning into a transparent solution;

step 2, dissolving sodium carboxymethylcellulose in the purified water in an amount accounting for 20% of the total amount of water used, adding glycerinum to obtain a mixed substance, and stirring the mixed substance at a constant temperature of 37° C. for 0.5 h to obtain a solution;

step 3, stirring and mixing the two solutions prepared in step 1 and step 2 respectively, adding the remaining 40% of purified water and the stabilizer to obtain a mixed solution, and stirring the mixed solution for 0.5 h;

step 4: adding the essence into the solution prepared in step 3 and stirring the solution until the essence is completely dissolved to obtain the composition.

Further, according to the method for preparation of the hydroxypropyl methyl cellulose-containing composition for treating esophageal mucosa, step 3 includes the sub-steps of: mixing the two solutions prepared in step 1 and step 2 by stirring to obtain a mixed solution, adding the remaining 40% of purified water into the mixed solution, adding the stabilizer, the xylitol, the sodium bicarbonate and the potassium hydroxide in turn to obtain a mixed material, stirring the mixed material at a temperature of 37° C. for 0.5 h, adding the citric acid obtain a mixed product, stirring the mixed product for 0.5 h, adding the phosphoric acid to adjust the pH value, adding the sodium benzoate when the pH value of the mixed product is within the range of 6.5-8.5 to obtain a mixed substance, and stirring the mixed substance homogeneously.

The sodium carboxymethylcellulose and the hydroxypropyl methyl cellulose used in combination have high adhesion and cohesiveness to the esophageal mucosa, and have dynamic viscosity in a range of 300~20,000 cP, thus ensuring that the sodium carboxymethylcellulose and the hydroxypropyl methyl cellulose can be well adhered to the esophageal mucosa when taken orally.

The composition of the invention is applied to the preparation of medicines for treating esophageal mucosa injuries.

The present invention has the following advantages:

(1) In the invention, the hydroxypropyl methyl cellulose generates a membrane in the esophagus to effectively shield the influences of harmful bacteria and hazardous environment to the mucosa, and the generated membrane has adhesion to the mucosa such that the membrane action is persistent.

(2) In the hydroxypropyl methyl cellulose-containing composition of the invention, the combination of the hydroxypropyl methyl cellulose and the sodium carboxymethylcellulose achieves a better membrane forming effect in the esophagus, and the generated membrane has higher adhesion to the mucosa and longer action duration, and can effectively improve the growth environment of bacteria.

(3) In the hydroxypropyl methyl cellulose-containing composition of the invention, glycerinum has a moisturizing effect, facilitating repair of the injured ulcer surfaces, and the effect of the glycerinum is also persistent, just like the formed membrane. The xylitol helps competitive exclusion of pathogens to form a biological barrier and protect the mucosa; besides, the polydextrose can also adsorb pathogenic bacteria and is capable of being strongly bonded with phytolectin on the surfaces of the bacteria, the pathogenic bacteria which are bonded with the polydextrose do not adhere to the wall of the esophagus; moreover, the pathogenic bacteria cannot obtain nutrients from the polydextrose, lack energy resources, finally die and are eliminated out of the human body.

(4) The hydroxypropyl methyl cellulose-containing composition of the invention is particularly suitable for working in complicated environment of the esophagus, and can adjust the pH value of the mucosa environment such that diseases are gradually relieved.

(6) According to the preparation method of the hydroxypropyl methyl cellulose-containing composition provided by the invention, the hydroxypropyl methyl cellulose-containing composition can be prepared, which has stable adhesion, good properties, and high storage stability.

DETAILED DESCRIPTION OF EMBODIMENTS

The invention is described in further detail below with reference to the embodiments.

Embodiment 1

1 g of hydroxypropyl methyl cellulose and 1000 g of purified water were measured. The hydroxypropyl methyl cellulose was added, by stirring, into the purified water in an amount which accounts for 40% of the total amount of water used to obtain a mixed material; the mixed material was continuously stirred until completely swelling and turning into a transparent solution; the remaining purified water was added to obtain a mixture; and the mixture was continuously stirred for 0.5 h to obtain the required product.

Embodiment 2

15 g of hydroxypropyl methyl cellulose and 1000 g of purified water were measured. The hydroxypropyl methyl cellulose was added, by stirring, into the purified water in an amount which accounts for 40% of the total amount of water used to obtain a mixed material; the mixed material was continuously stirred until completely swelling and turning into a transparent solution; the remaining purified water was added to obtain a mixture; and the mixture was continuously stirred for 0.5 h to obtain the required product.

Embodiment 3

28 g of hydroxypropyl methyl cellulose and 1000 g of purified water were measured. The hydroxypropyl methyl cellulose was added, by stirring, into the purified water in an amount which accounts for 40% of the total amount of water used to obtain a mixed material; the mixed material was continuously stirred until completely swelling and turning into a transparent solution; the remaining purified water was added to obtain a mixture; and the mixture was continuously stirred for 0.5 h to obtain the required product.

Animal Experiment 1

SD mice with a weight of 200-240 g were prepared. In this experiment, treated mice groups where the mice took medicines that were prepared in embodiments 1-3, a blank control group and a model control group were included. Each of the groups included 20 SD mice. The mice in four treated mice groups and in the model reference group were mice with an esophageal mucosa injuries, and the mice in the blank control group were healthy mice. The mice with the esophageal mucosa injuries were specifically injured using the steps of bending a syringe needle by about 0.5 mm, stretching the bent syringe needle into the esophagus of each of the mice and then injuring the esophagus by a length of 1-4 mm. The mice which did not bleed continuously after 24 h were successfully injured mice. Visual observation and scoring of the esophageal mucosa injuries. The length and width of each of the bleeding sections were measured using a vernier caliper under a stereo microscope or with naked eyes. The severity of the injuries represented by the width was far higher than that represented by the length, so double points were accumulated. See table 1 for the scoring standard.

TABLE 1

Scoring standard for visual observation on esophageal mucosa injuries of mice caused by edged tools

|  | Degree of injuries | | | |
| --- | --- | --- | --- | --- |
|  | 1 Point | 2 Points | 3 Points | 4 Points |
| Length of bleeding section (mm) | 1 | 2 | 3 | 4 |
| Width of bleeding section (mm) | 1 | 1.5 | — | — |

Total point = point of length + (point of width × 2)

The mice in the treated mice groups took the hydroxypropyl methyl cellulose-containing compositions prepared in embodiments 1-3, three times a day, 3 g each time. The mice in the blank control group took purified water, three times a day, 3 g each time.

The mice in the model control group took purified water, three times a day, 3 g each time.

The mice in the blank group took purified water, three times a day, 3 g each time.

The mice were normally fed for one week, put to execution and then dissected, followed by index observation: the degree of the esophageal mucosa injuries of each of the experimental groups was expressed using the occurrence rate of the injuries (%), the index of the accumulated points of the injuries, and the injuries suppression rate.

Occurrence rate of the injuries (%)=number of mice with an esophageal mucosa injuries in a certain group/the number of mice in that group×100%.

Index of the accumulated points of the injuries=total injuries points of a group/number of mice of that group.

Injuries suppression rate (%)=(A−B)/A×100% (A and B respectively were the accumulated points of injuries of the model group and the administrated mice groups). See table 2 for specific indexes.

TABLE 2

Indexes table

| Degree of injuries | Number of mice | Occurrence rate of the injuries (%) | Total points of the injuries (%) | Injuries suppression rate |
|---|---|---|---|---|
| Model control group | 20 | 100 | 65.5 | 5 |
| Blank group | 20 | 0 | — | — |
| Administrated mice group using the composition prepared in Embodiment 1 | 20 | 100 | 67.5 | 5.2 |
| dministrated mice group using the composition prepared in Embodiment 2 | 20 | 100 | 67 | 55.3 |
| dministrated mice group using the composition prepared in Embodiment 3 | 20 | 100 | 66 | 57.9 |

To the surprise of the applicant of the invention, hydroxypropyl methyl cellulose was dissolved in water and was capable of generating a membrane effect in animal esophagi to cure mucous injuries. Further, the effects of different amounts of the hydroxypropyl methyl cellulose were compared. A basic discipline was found that better effects were achieved with more hydroxypropyl methyl cellulose. The highest injuries suppression rate was obtained when the ratio of the hydroxypropyl methyl cellulose to the purified water was 15-28:1000. However, the effect became stable when the amount of the hydroxypropyl methyl cellulose was about 20 g, and the injury curing effect was enhanced slightly as the amount of the hydroxypropyl methyl cellulose increased. In subsequent experiments, the composition was accordingly studied and optimized.

Embodiment 4

1 g of hydroxypropyl methyl cellulose, 1 g of sodium carboxymethylcellulose, 30 g of glycerinum, 20 g of stabilizer, 0.1 g of essence, and 1000 g of purified water were measured. The hydroxypropyl methyl cellulose was added, by stirring, into the purified water which accounts for 40% of the total amount of water used to obtain a mixed material; the mixed material was continuously stirred until completely swelling and turning into a transparent solution; the sodium carboxymethylcellulose was dissolved in the purified water in an amount accounting for 20% of the total amount of water used, and was mixed with the glycerinum to obtain a mixed substance; and the mixed substance was stirred at a constant temperature of 37° C. for 0.5 h. The remaining purified water and the stabilizer were added to obtain a mixture; the mixture was stirred for 0.5 h; and then the essence was added and stirred to be completely dissolved to obtain the required product.

Embodiment 5

15 g of hydroxypropyl methyl cellulose, 5 g of sodium carboxymethylcellulose, 100 g of glycerinum, 10 g of stabilizer, 0.05 g of essence, and 1000 g of purified water were measured. The hydroxypropyl methyl cellulose was added, by stirring, into the purified water which accounts for 40% of the total amount of water used to obtain a mixed material; the mixed material was continuously stirred until completely swelling and turning into a transparent solution; the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h. The remaining purified water and the stabilizer were added to obtain a mixture; the mixture was stirred for 0.5 h; and then the essence was added and stirred to be completely dissolved to obtain the required product.

Embodiment 6

28 g of hydroxypropyl methyl cellulose, 10 g of sodium carboxymethylcellulose, 150 g of glycerinum, 0.3 g of stabilizer, 0.001 g of essence, and 1000 g of purified water were measured.

The hydroxypropyl methyl cellulose was added, by stirring, into the purified water which accounts for 40% of the total amount of water used to obtain a mixed material; the mixed material was continuously stirred until completely swelling and turning into a transparent solution; the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h. The remaining purified water and the stabilizer were added to obtain a mixture; the mixture was stirred for 0.5 h; and then the essence was added and stirred to be completely dissolved to obtain required product.

Embodiment 7

1 g of hydroxypropyl methyl cellulose, 1 g of sodium carboxymethylcellulose, 30 g of glycerinum, 50 g of sodium bicarbonate, 25 g of xylitol, 3 g of citric acid, 6 g of potassium hydroxide, 6 g of phosphoric acid, 1 g of sodium benzoate, 10 g of stabilizer, 0.05 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; and the transparent solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain required product.

Embodiment 8

5 g of hydroxypropyl methyl cellulose, 15 g of sodium carboxymethylcellulose, 100 g of glycerinum, 90 g of sodium hydrogen carbonate, 40 g of xylitol, 6 g of citric acid, 9 g of potassium hydroxide, 10 g of phosphoric acid, 2 g of sodium benzoate, 0.3 g of stabilizer, 0.001 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; and the transparent solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain the required product.

In this embodiment, 5 h of the auxiliary material, sodium carboxymethylcellulose, was added, and it was observed that the insulating performance and adhesion of the formed membrane were enhanced obviously.

Embodiment 9

10 g of hydroxypropyl methyl cellulose, 28 g of sodium carboxymethylcellulose, 150 g of glycerinum, 1 g of sodium hydrogen carbonate, 10 g of xylitol, 0.1 g of citric acid, 2 g of potassium hydroxide, 2 g of phosphoric acid, 0.1 g of sodium benzoate, 0.3 g of stabilizer, 0.001 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; and the transparent solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain the required product.

Embodiment 10

5 g of maltodextrin, 15 g of hydroxypropyl methyl cellulose, 100 g of glycerinum, 90 g of sodium hydrogen carbonate, 40 g of xylitol, 6 g of citric acid, 9 g of potassium hydroxide, 10 g of phosphoric acid, 2 g of sodium benzoate, 0.3 g of stabilizer, 0.001 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; and the transparent solution was stirred at a constant temperature of 37° C. for 1 h.

Step 2, the maltodextrin was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain the required product.

Embodiment 11

10 g of polydextrose, 1 g of sodium carboxymethylcellulose, 1 g of hydroxypropyl methyl cellulose, 30 g of glycerinum, 1 g of sodium hydrogen carbonate, 10 g of xylitol, 0.1 g of citric acid, 2 g of potassium hydroxide, 2 g of phosphoric acid, 0.1 g of sodium benzoate, 20 g of stabilizer, 0.1 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; the polydextrose was added in succession, and the obtained solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain the required product.

Embodiment 12

25 g of polydextrose, 5 g of sodium carboxymethylcellulose, 15 g of hydroxypropyl methyl cellulose, 100 g of glycerinum, 50 g of sodium hydrogen carbonate, 25 g of xylitol, 3 g of citric acid, 6 g of potassium hydroxide, 6 g of phosphoric acid, 1 g of sodium benzoate, 10 g of stabilizer, 0.05 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; the polydextrose was added in succession, and the obtained solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution. The essence was added into the solution prepared in step 3 and stirred to be completely dissolved to obtain the required product.

The polydextrose played a pharmaceutical assistance role, capable of enhancing the membrane-forming property. However, the result of this embodiment showed that the membrane-forming property of the composition was not obviously enhanced in comparison with the membrane-forming property of the sodium carboxymethylcellulose, while the stability of the composition declined. According to results of acceleration tests, the property was slightly changed within six months.

Embodiment 13

30 g of polydextrose, 10 g of sodium carboxymethylcellulose, 28 g of hydroxypropyl methyl cellulose, 150 g of glycerinum, 90 g of sodium hydrogen carbonate, 40 g of xylitol, 6 g of citric acid, 9 g of potassium hydroxide, 10 g of phosphoric acid, 2 g of sodium benzoate, 0.3 g of stabilizer, 0.001 g of essence, and 1000 g of purified water were measured.

Step 1, the hydroxypropyl methyl cellulose was added, by stirring, into the purified water in an amount which accounts for 40% of the total amount of water used to obtain a mixed material; the mixed material was continuously stirred until completely swelling and turning into a transparent solution; the polydextrose was added in succession, and the obtained solution was stirred at a constant temperature of 37° C. for 1 h.

Step 2, the sodium carboxymethylcellulose was dissolved in the purified water in an amount accounting for 20% of the total amount of water used, and added with the glycerinum to obtain a mixed substance; and the mixed substance was stirred at a constant temperature of 37° C. for 0.5 h.

Step 3, the two solutions prepared in step 1 and step 2 were mixed by stirring to obtain a mixed solution; the remaining 40% purified water was added into the mixed solution, followed by the stabilizer, the xylitol, the sodium bicarbonate and the potassium hydroxide to obtain a mixed material; the mixed material was stirred at a temperature of 37° C. for 0.5 h; then, the citric acid was added to obtain a mixed product; the mixed product was stirred for 0.5 h and then added with the phosphoric acid for adjusting the pH value, and the sodium benzoate was added when the pH value of the mixed product was within the range of 6.5-8.5 to obtain a substance, and the substance was stirred homogeneously to obtain a solution.

The essence was added into the solution prepared in step 3 and then stirred to be completely dissolved to obtain required product.

Animal Experiment 2

Experimental operations and scoring standards were identical with those in the animal experiment 1.

The mice in the first treated mice group took the hydroxypropyl methyl cellulose-containing composition prepared in embodiment 2, three times a day, 3 g each time. The mice in the second treated mice group took the hydroxypropyl methyl cellulose-containing composition prepared in embodiment 5, three times a day, 3 g each time. The mice in the third treated mice group took the hydroxypropyl methyl cellulose-containing composition prepared in embodiment 8, three times a day, 3 g each time. The mice in the fourth treated mice group took the hydroxypropyl methyl cellulose-containing composition prepared in embodiment 12, three times a day, 3 g each time.

The mice in the blank control group took purified water, three times a day, 3 g each time.

The mice in the model control group took purified water, three times a day, 3 g each time.

The mice were normally fed for one week, executed and dissected, followed by index observation. See table 3 for specific indexes.

TABLE 3

Indexes table

| Degree of injuries | Number of mice | Occurrence rate of the injuries (%) | Total points of the injuries (%) | Injury suppression rate |
|---|---|---|---|---|
| Model control group | 20 | 100 | 65. | 5 |
| Blank group | 20 | 0 | — | — |
| First administrated mice group | 20 | 100 | 67 | 55.3 |
| Second administrated mice group | 20 | 100 | 66.5 | 68.2 |
| Third administrated mice group | 20 | 100 | 67.5 | 69.8 |
| Fourth administrated mice group | 20 | 100 | 67.2 | 71.1 |

From table 3 it is known that the hydroxypropyl methyl cellulose-containing compositions prepared in embodiments 2, 5, 8 and 12 achieved a good effect on treating and caring the esophageal mucosa injuries. The composition in embodiment 8 has higher stability, and brings higher insulating performance and adhesion to the formed membrane.

The hydroxypropyl methyl cellulose-containing compositions prepared in embodiments 2, 5, 8 and 12 were given to patients with radiation esophagitis. 10 patients with radiation esophagitis (pains, esophageal mucosa injuries) took each of the compositions orally three times a day, 10 ml each time. A random control method was adopted, wherein the control group was given with the same amount of normal saline by the same application method (10 patients were selected). The medication administration proceeded for 3 consecutive weeks. Results showed that the hydroxypropyl methyl cellulose-containing compositions prepared in embodiments 2, 5, 8 and 12 achieved more obvious alleviation effects on the radiation esophagitis than the control group taking the normal saline did, and the symptoms of patients were obviously alleviated.

The present invention is described in detail through general notes and specific embodiments. On the basis of the present invention, some modifications and improvements can be made, which are obvious to those skilled in this field. Therefore, all modifications or improvements made on the basis of the concept of the present invention shall fall within the protective scope claimed by the present invention.

INDUSTRIAL APPLICABILITY

The invention discloses an application of hydroxypropyl methyl cellulose in preparation of medicines for treating esophageal mucosa. The invention also provides a hydroxypropyl methyl cellulose-containing composition which comprises the following ingredients: 1-28 weight parts of hydroxypropyl methyl cellulose and 1000 weight parts of purified water. A preparation method includes the steps of adding the hydroxypropyl methyl cellulose, by stirring, into the purified water in an amount which accounts for 40% of the total amount of water used to obtain a mixed material, continuously stirring the mixed material until the mixed material is completely swelling and turns into a transparent solution, adding the remaining purified water to obtain a mixture, and stirring the mixture to obtain the hydroxypropyl methyl cellulose-containing composition. The hydroxypropyl methyl cellulose and the hydroxypropyl methyl cellulose-containing composition in the invention generate a membrane in the esophagus, and the generated membrane has adhesion and therefore works continuously. The invention has a great application prospects.

What is claimed is:

1. A hydroxypropyl methyl cellulose-containing composition for treating esophageal mucosa, comprising: 1-28 parts by weight of hydroxypropyl methyl cellulose, 1-10 parts by weight of sodium carboxymethylcellulose or maltodextrin, 30-150 parts by weight of glycerinum, 0.3-20 parts by weight of stabilizer, 0.001-0.1 parts by weight of flavor and 1000 parts by weight of purified water;
wherein the composition further comprises: 1-90 parts by weight of sodium bicarbonate, 10-40 parts by weight of xylitol, 0.1-6 parts by weight of citric acid, 2-9 parts by weight of potassium hydroxide, 2-10 parts by weight of phosphoric acid, 0.1-2 parts by weight of sodium benzoate and 10-40 parts by weight of polydextrose.

2. The hydroxypropyl methyl cellulose-containing composition of claim 1, wherein the stabilizer is polysorbate, sorbitol fatty acid esters, monoacylglyceride, Arabic gum, gelatin or yolk, or a combination thereof.

3. The hydroxypropyl methyl cellulose-containing composition of claim 1, comprising: 5 parts by weight of sodium carboxymethylcellulose, 15 parts by weight of hydroxypropyl methyl cellulose, 100 parts by weight of glycerinum, 0.3 part by weight of stabilizer, 0.001 part by weight of the flavor, 1000 parts by weight of purified water, 90 parts by weight of sodium bicarbonate, 40 parts by weight of xylitol, 6 parts by weight of citric acid, 9 parts by weight of potassium hydroxide, 10 parts by weight of phosphoric acid, and 2 parts by weight of sodium benzoate.

4. A method for preparing the hydroxypropyl methyl cellulose-containing composition of claim 1, comprising:
step 1, adding the hydroxypropyl methyl cellulose, by stirring, into the purified water in an amount which accounts for 40% of the total amount of water used to obtain a mixed material, continuously stirring the mixed material until the mixed material completely swells and turns into a transparent solution; and adding the polydextrose to the transparent solution followed by stirring at 37° C. for 0.5 h;
step 2, dissolving the carboxymethylcellulose sodium in the purified water in an amount accounts for 20% of the total amount of water used, adding the glycerinum to obtain a mixed substance, and stirring the mixed substance at a constant temperature of 37° C. for 0.5 h to obtain a solution;
step 3, stirring and mixing the two solutions prepared in step 1 and step 2 respectively, adding the remaining 40% of purified water and the stabilizer to obtain a mixed solution; adding the stabilizer, the xylitol, the sodium bicarbonate and the potassium hydroxide sequentially to obtain a mixed material, stirring the mixed material at 37° C. for 0.5 h, adding the citric acid to obtain a mixed product, stirring the mixed product for 0.5 h, adjusting pH to 6.5-8.5 with phosphoric acid, adding the sodium benzoate to obtain a mixed substance, and stirring the mixed substance homogeneously; and step 4: adding the flavor into the solution prepared in step 3 and stirring the solution until the flavor is completely dissolved to obtain the composition.

\* \* \* \* \*